(12) United States Patent
Nyfors

(10) Patent No.: US 10,060,869 B2
(45) Date of Patent: Aug. 28, 2018

(54) SYSTEM FOR MEASURING CHARACTERISTICS OF A FLUID FLOW

(71) Applicant: Roxar Flow Measurement AS, Stavanger (NO)

(72) Inventor: Ebbe Gustaf Nyfors, Sandnes (NO)

(73) Assignee: Roxar Flow Measurement AS, Stavanger (NO)

( * ) Notice: Subject to any disclaimer, the term of this patent is extended or adjusted under 35 U.S.C. 154(b) by 0 days.

(21) Appl. No.: 15/556,522

(22) PCT Filed: Apr. 15, 2016

(86) PCT No.: PCT/EP2016/058338
§ 371 (c)(1),
(2) Date: Sep. 7, 2017

(87) PCT Pub. No.: WO2016/169847
PCT Pub. Date: Oct. 27, 2016

(65) Prior Publication Data
US 2018/0045662 A1 Feb. 15, 2018

(30) Foreign Application Priority Data
Apr. 23, 2015 (NO) .................................. 20150495

(51) Int. Cl.
*G01N 27/04* (2006.01)
*G01N 33/28* (2006.01)
(Continued)

(52) U.S. Cl.
CPC .............. *G01N 27/04* (2013.01); *G01N 22/04* (2013.01); *G01N 33/0036* (2013.01); *G01N 33/18* (2013.01); *G01N 33/2847* (2013.01)

(58) Field of Classification Search
CPC ......... G01N 22/04; G01F 1/74; F16L 55/0336
See application file for complete search history.

(56) References Cited

U.S. PATENT DOCUMENTS 6,466,035 B1   10/2002   Nyfors et al.
6,915,707 B2    7/2005   Nyfors et al.
(Continued)

FOREIGN PATENT DOCUMENTS

EP    2500699 B1    3/2015
NO     308922 B1   11/2000
(Continued)

OTHER PUBLICATIONS

Savage, John, "International Search Report," prepared for PCT/EP2016/058338, dated Jun. 29, 2016, four pages.
(Continued)

*Primary Examiner* — Jermele M Hollington
*Assistant Examiner* — Alvaro Fortich
(74) *Attorney, Agent, or Firm* — Winstead PC

(57) ABSTRACT

The present invention relates to a system for measuring electrical characteristics of a fluid flowing through a section of a pipe, the system comprising a coaxial resonator, formed by an essentially coaxial insert in said pipe defining an annular volume between a chosen part of said insert and the pipe wall, said insert and pipe wall being made from an electrically conductive material, the system further comprising at least one antenna adapted to emit electromagnetic signals into and receive electromagnetic signals from said coaxial resonator, and means to measure the frequency response of said coaxial resonator within a frequency range including the waveguide mode $TE_{11}$ of said coaxial resonator, The coaxial insert is mounted to the pipe wall through at least one support leg being positioned outside said annular volume, and one electrically conductive fin is positioned at least partially in the annular volume, said fin being positioned in a radial plane, said plane being different from the plane of said at least one antenna and the axis of said annular volume.

12 Claims, 7 Drawing Sheets

(51) Int. Cl.
*G01N 22/04* (2006.01)
*G01N 33/00* (2006.01)
*G01N 33/18* (2006.01)

(56) References Cited

U.S. PATENT DOCUMENTS

| | | | | |
|---|---|---|---|---|
| 2004/0244501 A1* | 12/2004 | Nyfors | .................. | G01F 1/40 |
| | | | | 73/861.63 |
| 2005/0188771 A1* | 9/2005 | Lund Bo | .................. | G01F 1/40 |
| | | | | 73/861 |
| 2012/0006430 A1* | 1/2012 | Gentile | .................. | G01F 1/40 |
| | | | | 137/561 R |

FOREIGN PATENT DOCUMENTS

| | | |
|---|---|---|
| NO | 315584 B1 | 9/2003 |
| WO | WO-2007/089156 A1 | 8/2007 |
| WO | WO-2010115883 A1 | 10/2010 |
| WO | WO-2014122093 A1 | 8/2014 |

OTHER PUBLICATIONS

Nyfors, E., "Cylindrical Microwave Resonator Sensors for Measuring Materials Under Flow," Thesis for degree of Doctor of Science in Technology, Helsinki University of Technology, Radio Laboratory, Report S243, 2000, 181 pages.

\* cited by examiner

SYSTEM FOR MEASURING CHARACTERISTICS OF A FLUID FLOW

This invention relates to a measuring system for measuring the characteristics of a fluid flow, especially a multiphase fluid flow comprising a fraction of water.

In oil and gas production and processing it is necessary to monitor the content and properties of the fluid flow as the fractions of oil, gas and water and the salinity of the water will change during the production and will affect the further processing. Several types of technology have been used to sample the information necessary to find the fractions and the salinity, such as acoustic measurements, pressure, gamma and electrical measurements.

The present invention relates to electrical measurements used to determine the content in mixtures of oil, gas, and water and specifically the conductivity of the water of the flow, thus indicating the salinity and/or the water content in the flow. Dissolved salts in the water gives the water conductivity. This may be measured as the salinity will affect the conditions for electromagnetic signals in or close to the microwave range, and more specifically in the effect of resonance frequencies of the electromagnetic signals in the flow, as is discussed in the publications discussed below.

The conductivity depends on the amount and type of ions in the solution, and the temperature. The water in a multiphase flow in the oil industry may contain several types of ions, but the by far most common are Na+ and Cl− from sodium chloride. By salinity we here mean the equivalent amount of sodium chloride, which gives the same conductivity as the actual solution, and it is expressed in % weight of the saline water.

Several types of inserts in pipes are known for providing conductivity measurements on fluid flows. European patent EP2500699B1 describes a conical insert for this purpose where the supporting fins are shaped so as not to have influence on the measurements while providing enough mechanical stiffness for avoiding vibrations. The measurements in EP2500699B1 are based on a microwave resonance peak in the coaxial resonance mode, the electromagnetic fields of which are symmetric around the insert and the sensitivity to variations in conductivity in the circular space will be limited. For simplicity the word microwave is used here as a general term for all high frequency signals without specific frequency limits, comprising also what might otherwise be called e.g. RF or millimeter waves.

In WO2014/122093 a solution is discussed aimed at improving the conductivity measurements by providing and measuring the electromagnetic field at two resonances in terms of the resonant frequencies and Q-factors. The different resonant frequencies in WO2014/122093 may be obtained in several different ways. One of them may be the coaxial TEM mode discussed in EP2500699B1, while others may be higher order resonances of the TEM-mode, or so-called waveguide modes (see below) obtained by constructing the insert or placing probes comprising antennas or transducers in a specific way.

NO315584/U.S. Pat. No. 6,915,707 describes a multiphase measurement utilizing TE11 and TEM modes to measure the frequency response of the medium, while NO308922/U.S. Pat. No. 6,466,035 describes a microwave sensor for measuring the ratio between several fluids flowing in a pipe, where the sensor is provided with a radial, electrically conductive fin extending along the pipe axis, possibly inside the measured volume.

In general electromagnetic energy can propagate in hollow waveguides (e.g. rectangular or circular waveguides) as wave modes, which each he a specific field pattern, which fulfils the boundary conditions. There is in theory an infinite number of possible wave modes. They are divided in two groups, $TE_{nm}$ and $TM_{nm}$ modes. A specific feature for wave modes in hollow waveguides is that each mode has a cutoff frequency, which means that it can only propagate at frequencies above that frequency. The cutoff frequency of $TM_{nm}$ in a circular waveguide is given by $$f_{c,nm} = \frac{cp_{nm}}{2\pi a} \qquad (1)$$

where c is the speed of light, a is the (inner) radius of the pipe, and $p_{nm}$ is a constant specific for the mode. The same equation applies for $TE_{nm}$ modes, but then the constant p is marked with a prime. The p-values can be found in tables in microwave textbooks, and also e.g. in the thesis [1] by Nyfors, E., "Cylindrical microwave resonator sensors for measuring materials under flow", Thesis for degree of Doctor of Science in Technology, Helsinki University of Technology, Radio Laboratory, Report S 243, 2000, 181p., which also explains the basic features of waveguide modes.

One of the modes has the lowest cutoff frequency of them all. It may be shown (see the Table 5.3 in the Nyfors thesis mentioned above) that the smallest p value is 1.8412, and belongs to the mode $TE_{11}$. For a circular waveguide with an inner diameter of 125 mm Eq. (1) then gives 1406.6 MHz as the cutoff frequency. Below that frequency no electromagnetic waves can propagate. However, this applies for "vacuum", or an air-filled waveguide. With another medium the cutoff frequency changes in the same way as the resonant frequency of a cavity resonator.

A structure with more than one conductor, like a coaxial cable, can support a third type of mode, a TEM mode. This mode has no cutoff frequency. Coaxial structures can, however, also support waveguide modes, which have a cutoff frequency. The first waveguide mode in a coaxial structure is also called $TE_{11}$, even though it is a different mode than the mode with the same name in a circular waveguide. The cutoff frequency of the coaxial waveguide mode $TE_{11}$ is approximately $$f_{c,11} = \frac{c}{\pi(a+b)} \qquad (2)$$

where a and b are the radii of the inner and outer conductor. Again a dielectric medium reduces the cutoff frequency.

General note for using coaxial cables or waveguides for carrying modulated signals e.g. for communication purposes: Waveguide modes propagate with a group velocity dependent on the ratio between the frequency and the cutoff frequency:

$$v_g = v_{pw}\sqrt{1 - \left(\frac{f_c}{f}\right)^2} \qquad (3)$$

where $v_{pw}$ is the velocity of a plane wave (i.e. in free space). TEM waves, which have no cutoff frequency, propagate with the same velocity as plane waves. If several modes can propagate in a transmission line (waveguide, coaxial cable) at the used frequency, energy may leak over from one mode to another at discontinuities, bends, etc. Because waveguide modes propagate with a lower group velocity than plane waves, e.g. the $TE_{11}$ mode in a coaxial cable propagates more slowly than the TEM mode. In most situations, where coaxial cables are used for carrying signals, this would lead to unacceptable dispersion effects. Therefore a coaxial cable has in practice an upper frequency limit equal to the cutoff frequency of $TE_{11}$, and cables for high frequencies are small in diameter. Of the same reason waveguides are used in the frequency range, where only the first mode can propagate. For common rectangular waveguides this range is one octave.

A microwave resonator in a pipe can be thought of as being a section of transmission line (e.g. hollow waveguide or coaxial structure) with reflecting ends. A resonance mode is based on a propagating wave mode. Resonance occurs, when the reflections create a standing wave pattern.

When a resonator sensor is designed in a pipe such that the resonant frequency is below the cutoff frequency of the pipe as a waveguide, the energy stored in the resonance cannot escape by propagation. Then a relatively open structure can be used as no grids or other highly intrusive structures are needed to contain the energy. To achieve this, the transmission line must be able to support waves at lower frequencies than the pipe, i.e. have a lower cutoff frequency than the pipe. A coaxial structure fulfils the criterion as the TEM mode has no cutoff frequency. Also sectorial or semisectorial structures fulfill the criterion, as described in [1].

The cone resonator is a coaxial structure, where the energy is contained in the resonator mainly because the resonant frequency is below the cutoff frequency of the pipe, which means that the stored energy cannot leak away from the resonator by propagating in the pipe. This criterion is automatically fulfilled for the resonance used for permittivity measurement with the cones discussed in EP2500699B1, where the cone legs continue some distance up on the cone, which makes it mechanically more robust. The broad head of the cone therefore protrudes resulting in a coaxial structure. The cone is the centre conductor and the pipe the outer conductor. The legs act as a short circuit, while the other end is an open circuit. Therefore the first resonance of the basic TEM mode will be a $\lambda/4$-type resonance (see Sec. 3.3 in [1]). The electric field is radial and circularly symmetrical. The electric field maximum is in the broad open-circuited end of the cone, and it is zero in the end of the legs. Because of the conical shape the mode is capacitively loaded in the open end, which makes the resonant frequency lower than it would be if calculated simply from the wavelength being four times the protruding length of the cone. Because of the link between the wavelength and the length of the cone it is clear that a longer cone has a lower resonant frequency.

There will also be higher order resonances based on the TEM mode, the next one being of the $3\lambda/4$ type, but with any practical cone design the resonant frequency is above the cutoff frequency of the pipe. The energy may therefore propagate in the pipe and the resonance is useless for measuring purposes.

The present invention relates to a solution where the first resonance of the coaxial $TE_{11}$ waveguide mode is used as the second resonance for implementing the method described in WO2014/122093. The $TE_{11}$ mode has a field pattern with an amplitude variation over the circumference between the insert and the pipe wall. As will be discussed below the field pattern of the $TE_{11}$ mode will, under stable conditions, be positioned so as to provide maximum amplitude at the same position. But the mode may exist with any axial orientation, and once the symmetry in the flow conditions is changed, the positiones of the maxima may change, thus affecting the accuracy of the measurements.

It is an object of the present invention to provide a solution where the position of the $TE_{11}$ mode is maintained, especially in a system based on simultaneous measurements of the TEM and $TE_{11}$ resonance peaks. This is obtained as stated in the independent claims.

The invention will be discussed below with reference to the accompanying drawings, illustrating the invention by way of examples.

Figure 3A:
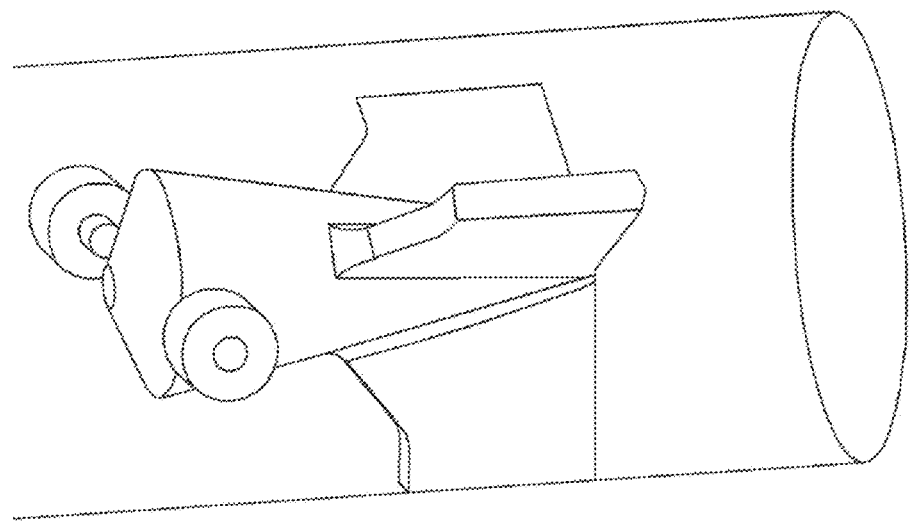
Figure 3A:
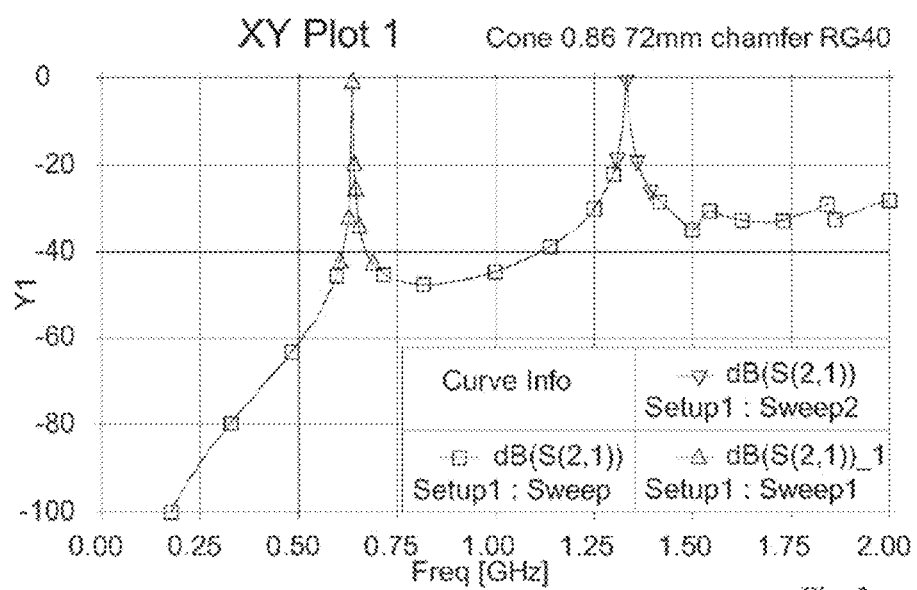

FIG. 3a, b illustrates a simulation of an empty resonator 3a and a segment of salt water placed asymmetrically to the antennas 3b.

Figure 4:
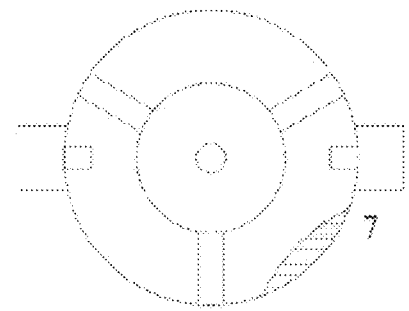
Figure 4:
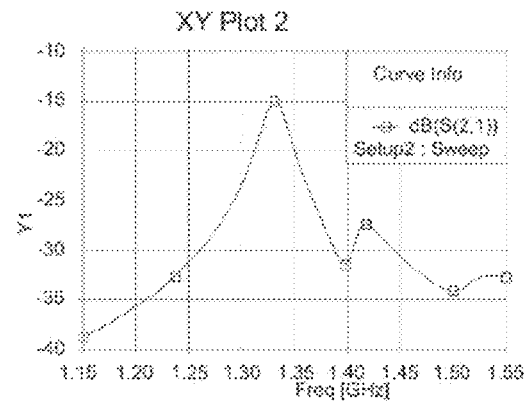
Figure 4:
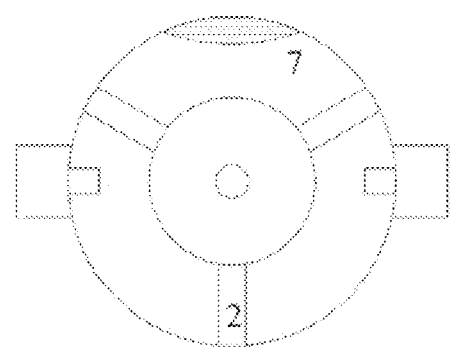
Figure 4:
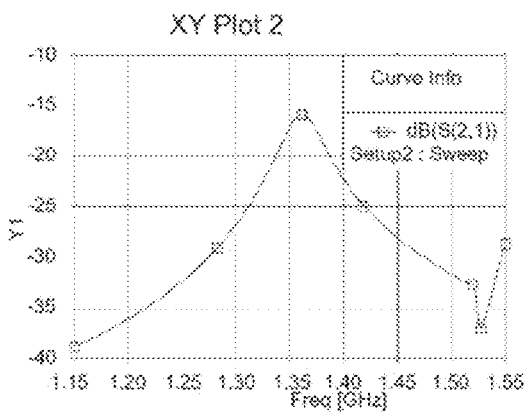
Figure 4:
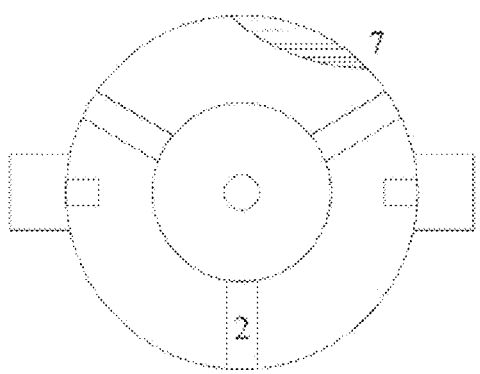
Figure 4:
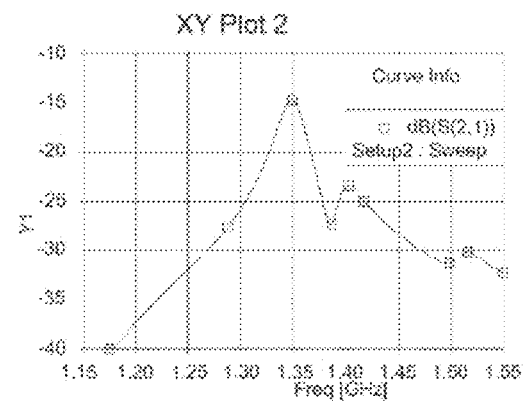

FIG. 4 illustrates the dependency of the position of the salt water on the resonance frequency conditions.

Figure 5:
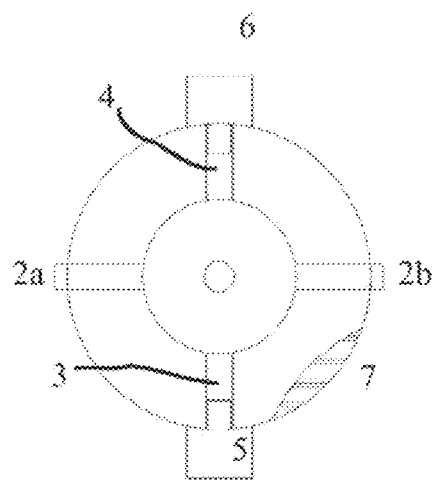
Figure 5:
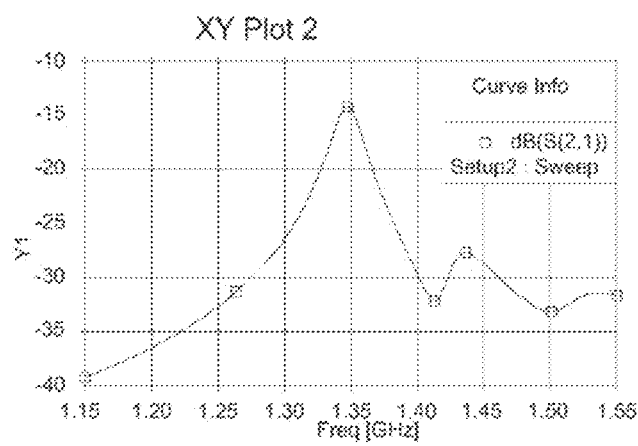
Figure 5:
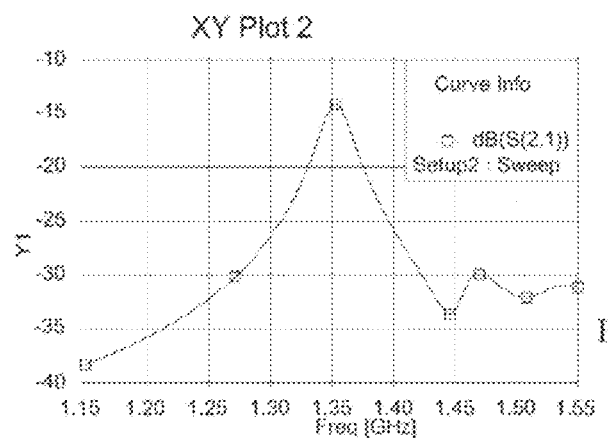

FIG. 5 Simulation results for a cone with 72 mm protrusion and 4 legs, of which 2 (the horizontal ones in the figure) are extended axially.

Figure 1:
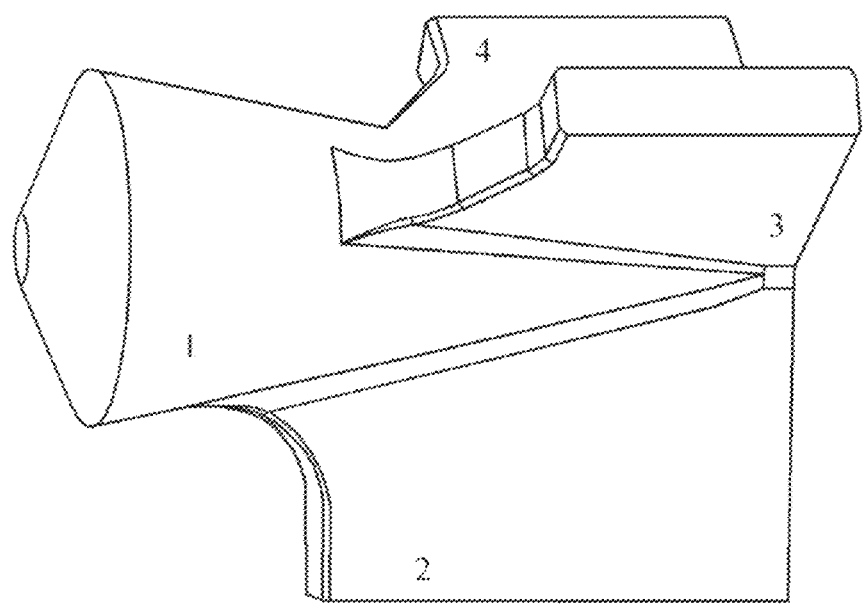
FIG. 1 illustrates a preferred embodiment of the present invention.

In FIG. 1 an embodiment of the present invention is shown constituted by a conical insert 1 having three support fins or legs 2, 3, 4 for mounting it to the pipe wall. One of the support legs 2 extend closer to the conical part than the others. The cone itself may have different variations in shape being more or less conical, depending on constructional choices and also affecting the resonant frequencies. There may also be more than three support legs, in which case there may also be two support legs, which extend closer to the conical part. These two legs must then be positioned essentially on opposite sides of the structure, i.e. with an angle close to 180° between the legs.

The coaxial waveguide mode $TE_{11}$ discussed above can propagate above the cutoff frequency given by Eq. (2), and exhibit resonances in the same way as the TEM mode.

The main difference is that the resonant frequency cannot be lower than the cutoff frequency of the mode, no matter how long the protruding cone would be, while the resonant frequencies of the TEM mode resonances continuously drop with increasing length. This is because the wavelength in a waveguide is $$\lambda_{wg} = \frac{\lambda_{pw}}{\sqrt{1-\left(\frac{f_c}{f}\right)^2}} \quad (4)$$

where $\lambda_{pw}$ is the wavelength of the plane wave. The wavelength $\lambda_{wg}$ is very long close to cutoff, and infinite at the cutoff frequency. There is therefore a fundamental limit to how low the first resonant frequency of the coaxial $TE_{11}$ mode can be. Eq. (2) shows that this limit depends on the radius a of the cone, but the radius varies along the cone. The limit (effective cutoff frequency) therefore depends on both the β ratio and the conical profile of the cone. The β ratio is a constant commonly used to describe the constriction provided by a venturi tube or a cone used for measuring flow by the differential pressure caused by the constriction, and is therefore a measure of the size of the cone compared to the diameter of the pipe. As it turns out the resonant frequency of the $TE_{11}$ mode, which will generally be called the second peak, is close to the cutoff frequency of the pipe for all practical cone designs. In the development work in a performed project attention was therefore paid to achieving a low enough second resonant frequency, while fulfilling all other requirements. The focus was on a design with β=0.86, as an example of a challenging case, because this value corresponds to a very small cone. If the same type of cone design is applied to larger cones in other cases, the second peak will have a larger margin to the cutoff frequency of the pipe.

Figure 2A:
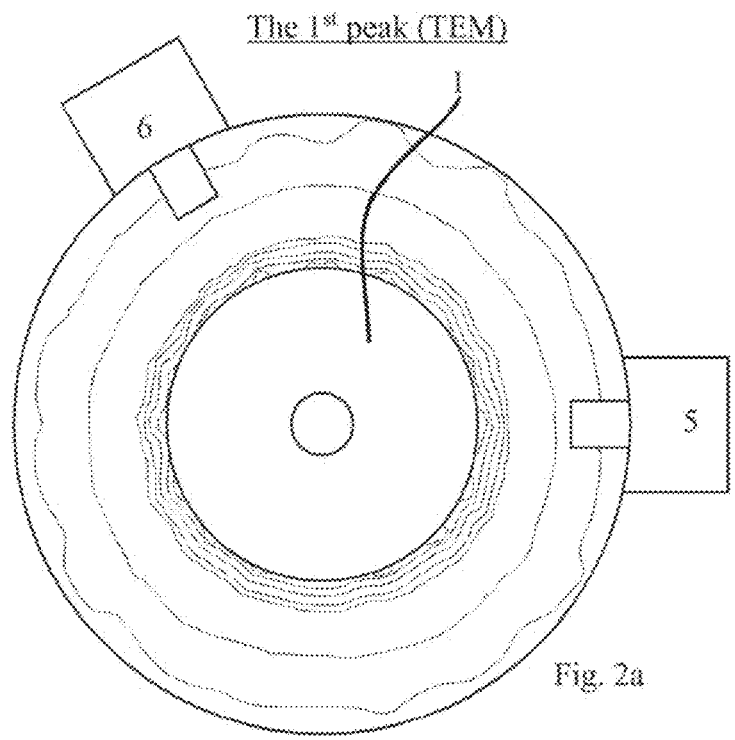
FIG. 2 illustrates the electrical field relative to a conical insert.

While the electric field pattern of the coaxial TEM mode is radial in the cross section of the coaxial structure and circularly symmetrical, that of the coaxial $TE_{11}$ mode varies along the circumference such that there are maxima (in opposite phase) on opposite sides of the structure and half way between (at 90° angles to the maxima) the field is zero. The orientation of the mode is determined mainly by the location of the antennas 5, 6. FIGS. 2*a*, *b* illustrates a cross section simulation of the electric field distribution of the two resonance modes, while FIGS. 2*c*, 2*d* illustrates a longitudinal section. Note the angular variation and the axial extension of the field of the second peak.

Figure 2B:
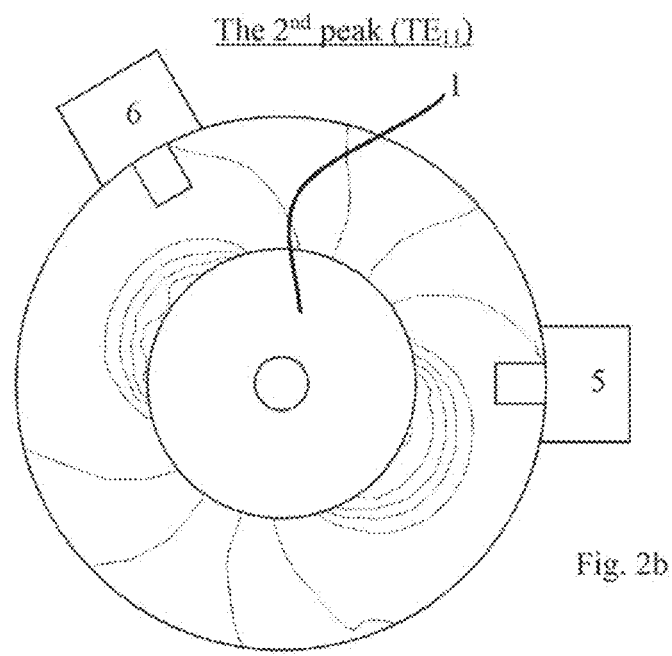
Figure 2C:
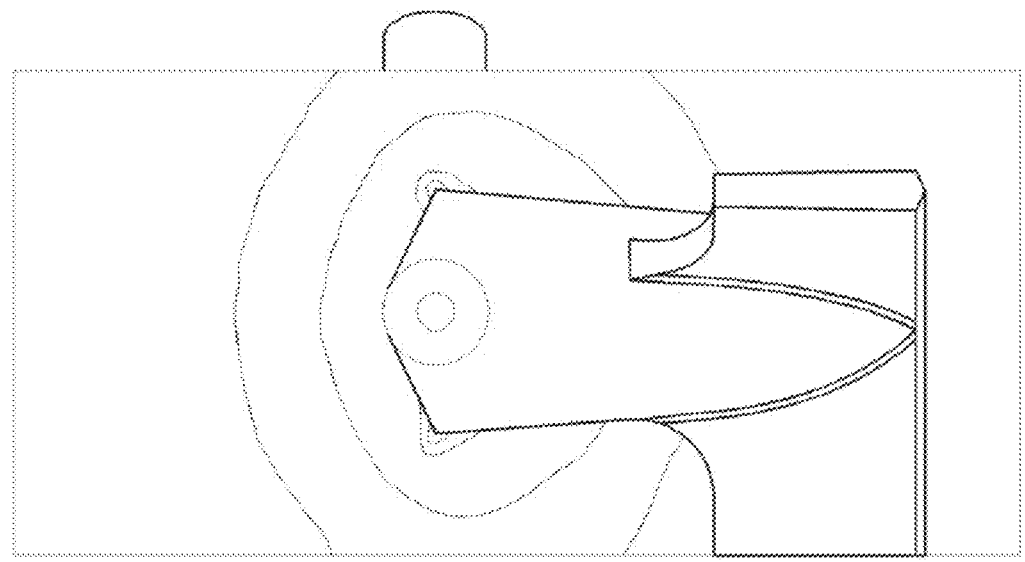
Figure 2D:
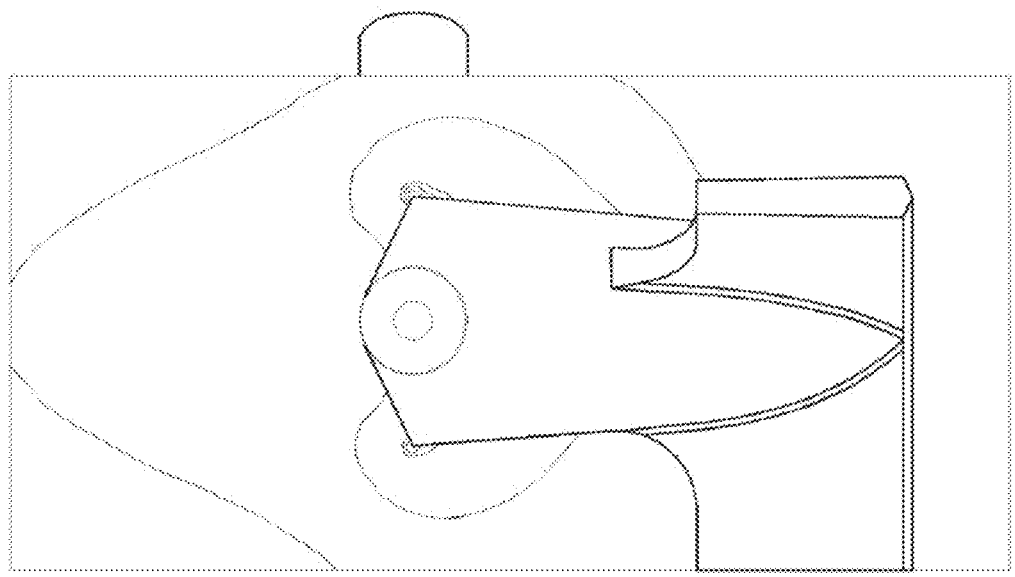

As mentioned above, because the field pattern of the coaxial $TE_{11}$ mode in FIGS. 2*b*, 2*d* is not circularly symmetrical, the same mode can exist with varying orientation. Particularly, two so-called orthogonal modes can exist independent of each other. The term "orthogonal" means that there is no coupling between the energy of the modes. In our case it also means that the field pattern of the orthogonal modes is turned 90° relative to each other. Both modes have their own resonances. Because everything is identical except for the orientation, the resonant frequencies are also the same. When several resonance modes have the same resonant frequency, they are called degenerate modes. Clearly the coaxial $TE_{11}$ mode will have two degenerate resonances in a circularly symmetrical structure.

Figure 3B:
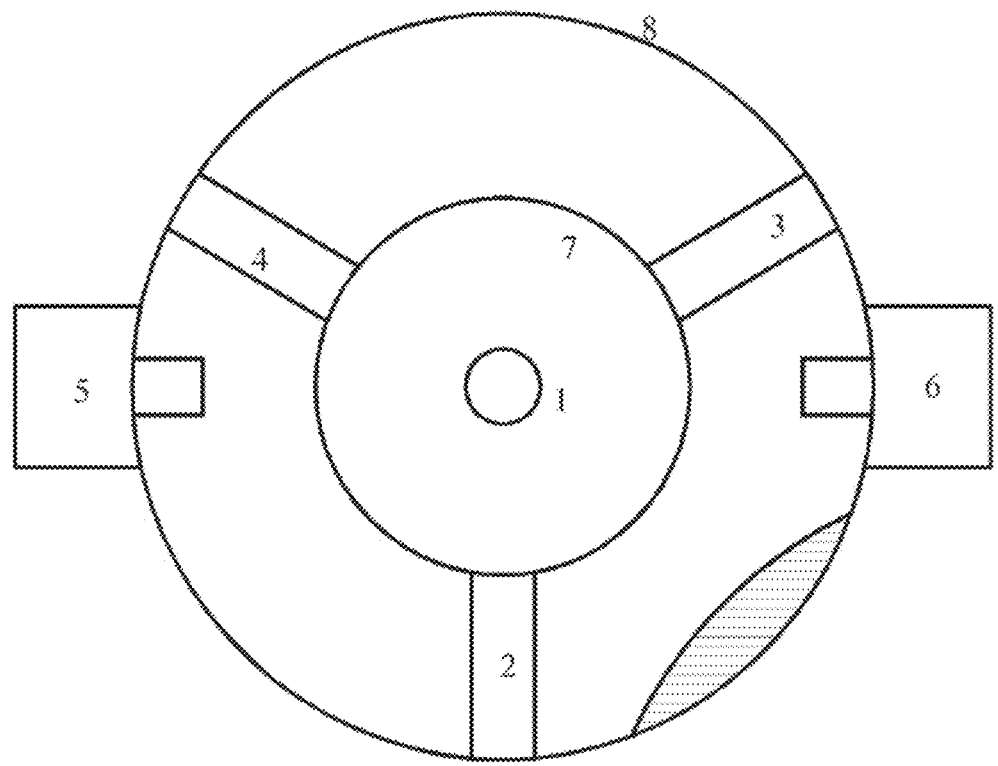
Figure 3B:
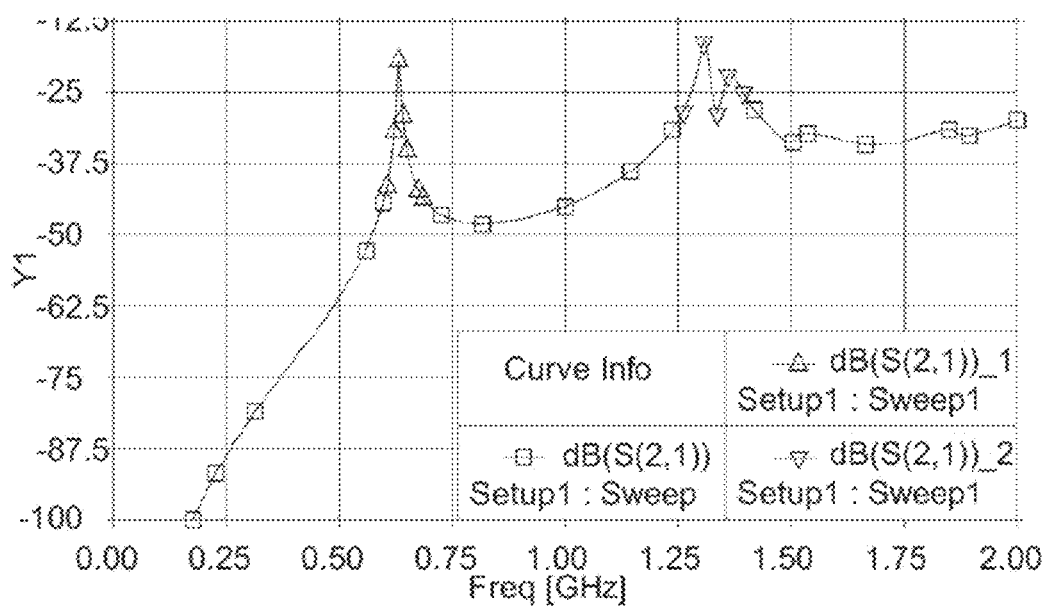

Degenerate resonance modes would easily cause problems in this type of applications. If both are excited and received, they will interfere and distort the resonance peak, as seen in FIGS. 3*a* and 3*b*. The effect will be largest on the measurement of the Q-factor. Especially if the distribution of permittivity (e.g. the distribution of water) in the wet gas flow is slightly uneven such that there is more water closer to a field maximum of one of the modes than the other, the one which "sees" more water experiences a larger change in the resonant frequency. Then the modes do not have exactly the same resonant frequency any more, and the interference is stronger. In a case of perfect circular symmetry, and the coupling antennas mounted on opposite sides of the pipe, only one of the degenerate modes would be excited, but an uneven distribution of permittivity also distorts the field pattern of the modes and thereby affects the coupling to the modes, and energy leaks over from one mode to the other. It is therefore not possible in practice to completely avoid the excitation of the unwanted degenerate mode by this antenna configuration alone. Clearly, the existence of degenerate modes makes the use of the second peak for measurement purposes challenging because the peak easily becomes corrupt because of interference. This is serious because the main reason for using the second peak is for measuring salinity using the method discussed in WO2014/122093, which is based on measuring the Q-factor at two frequencies, and as even a mild distortion has a strong effect on the Q-factor. It is an objective of the invention to avoid the problems caused by degenerate modes.

The shape of the electric field in the cross section of the second peak is shown in FIG. 2*b,d*. There are two maxima on opposite sides with zeros in the orthogonal directions. The mechanical structure with three identical supporting legs can be considered to be circularly symmetrical even though the legs do not cover the whole cross section, which means that the mode can exist with any orientation. Particularly there may be two orthogonal modes, as described above. With an angle between two antennas of 120° (as in FIG. 2), there will be even stronger interference between the modes than shown in FIG. 3. The interference must be eliminated, or at least strongly reduced before the peak can be used for measurement purposes.

One solution to eliminate the interference in a symmetric case is to change the antenna angle to 180°, and place them symmetrically relative to the legs, i.e. so that one half of the pipe is the mirror image of the other half. Simulations showed that the peak would be clean, i.e. free of interference, when the sensor was empty. However, it was clear that any asymmetry would distort the field distribution so that the orthogonal mode would be excited and received. To test the severity of the problem simulations have been performed with a segment of seawater 7 along the wall 8 placed asymmetrically as shown in FIG. 3*b*. The responses in the figure clearly show that the peak has become double because of strong interference.

Practical tests were also performed with a cone prototype welded in a piece of pipe. The antenna angle was 180°. The pipe was held in an angle roughly 20° off vertical and small amounts of water were poured through the sensor along the wall on one side, while the resonance peak was measured with a network analyzer. This also showed that the peak easily got distorted or even double. Of course both the simulation and this test were worst case scenarios, but the conclusion was that this alone is not a good enough solution.

When a mode has a radial plane of zero electric field, a metal sheet could be inserted in that plane without affecting the mode, because the boundary conditions would not be violated. This means that if one of the legs is a fin extended in the axial direction towards the broad end of the cone, the mode $TE_{11}$ can exist as before (even though the leg is quite thick), but only oriented such that the field maxima are in the direction perpendicular to the plane of the extended leg. The extended fin therefore locks the orientation of the mode. We can call this the primary mode, because it is the wanted mode. The orthogonal secondary (unwanted) mode can still exist in the region downstream of the extended leg or fin, flow direction being from right to left in FIG. 1. Even though only one fin is extended, and this therefore is not a well defined plane of short circuit, the effective length of the resonator is shorter for the secondary mode than for the primary one. It must be recalled that the resonant frequency based on the wave mode $TE_{11}$ depends on the cutoff frequency described by Eq. (2), and the wavelength described by Eq. (4), considering that the resonator is of the type $\lambda_{wg}/4$. The difference in effective length therefore separates the two modes in frequency.

With the extended fin the orthogonal wave modes no longer have degenerate resonance modes, but the distance between the peaks has to be large enough to avoid interference. The separation obviously also depends on the amount by which the fin is extended, which creates the difference in effective length of the resonators. For the primary mode $TE_{11}$ the fin could be extended even all the way to the downstream end of the cone, in which case the secondary mode would disappear completely, but so would the first peak because the TEM mode cannot exist. Extending the fin also moves the effective plane of short-circuit for the first peak resulting in a higher frequency. This is, however, not critical if the extension is small enough.

Some simulations were performed to find a good enough compromise. FIG. 4 shows the results for water 7 with a salinity roughly equivalent to that of seawater in different locations with a structure where the protruding part of the cone is 72 mm. The leg 2 (the one pointing downwards in the figure) extension is 30 mm. The antenna angle is also 180° to reduce the coupling to the secondary mode as much as possible. It is clear that the peak of the primary mode has been affected by the proximity of the secondary peak and the varying separation, which depends on the extent to which the two modes are affected by the water. This would not be good enough in a practical situation, but again the amount and extremely uneven distribution of the water is an exaggeration of a worst case. As the results also confirm the separation in frequency, this was concluded to be a good compromise of design parameters.

A more efficient separation of the two modes can be achieved with the same amount of extension by instead of three legs having four 2a,2b,3,4 or more, of which two opposite legs 2a,2b are extended. The two legs 2a,b would result in a more clearly defined plane of short-circuit for the secondary mode. This was also simulated, and the results are shown in FIG. 5. illustrating simulation results for a cone with 72 mm protrusion and four legs, of which two 2a,2b (the horizontal ones in the figure) are extended axially. In the upper case the extension is 20 mm, and 30 mm in the lower case. The results show that the separation is better than with three legs. They show roughly that the same amount of separation can be achieved with an extension of 20 mm as with an extension of 30 mm with the three-legged version. The four-legged version would clearly be a better alternative, but it is more expensive, creates more obtrusion to the flow, and is more difficult to weld.

Based on the discussion above, for the pipe and cone size used as an example in the description above, the preferred embodiment of the invention may thus be described as a 3-legged design with typically a 30 mm extension of one leg, and a antenna angle of 180°, the antennas being located 90° from the extended leg.

Another preferred embodiment is a 4-legged design with two opposite legs extended by typically 20 mm, and a antenna angle of 180°, the antennas being located 90° from the extended legs.

In the description above two coupling antennas 5,6 were assumed. It must, however, be understood that this is just an example. An engineer skilled in the art knows that also other numbers of antennas can be used without deviating from the invention. Resonators can e.g. also be measured using only one antenna, in which case the resonant frequency and Q-factor are found from the measured reflection coefficient, as explained in Ch. 3 of [1]. It is also possible to use more than two antennas, e.g. three antennas and e.g. detect the resonant frequency and Q-factor from the differential phase or amplitude measured by two receiving antennas. The problem of degenerate modes and the solution using extended leg(s) is the same regardless of the number of antennas used.

From the description above it became clear that the main effect of extending one or two legs was to create planes of short circuit at different places for the two orthogonal coaxial $TE_{11}$ resonance modes thereby separating them in frequency. The only requirement for creating the short circuit at the desired location is, however, the presence of the edge of the fin facing the volume, where the resonance exists, because this edge will define the position of the short circuit. The same effect can therefore also be achieved with a conducting post or any other structure connecting the insert (e.g. a cone) with the pipe wall thereby creating the short circuit at the desired location. It does not therefore need to be connected to any leg, and does not even need to be mounted in the same direction as any of the legs, but the orientation will define the orientation of the desired $TE_{11}$ resonance mode. The solution with an extended fin (or two) was chosen above only of practical reasons as an example, but is not the only possibility for creating planes of short circuit at different locations for modes with different orientation.

To summarize the present invention relates to a system for measuring electrical characteristics of a fluid flowing through a section of a pipe. The system comprising a coaxial resonator, formed by an essentially coaxial insert in said pipe defining a cylindrical or annular volume between a chosen part of said insert and the pipe wall, where the insert and pipe wall being made from an electrically conductive material. The system further comprising at least one probe with antenna adapted to emit electromagnetic signals into the coaxial resonator, and also to receive signals from the resonator so as to be able to measure the resonance properties in the volume. This may include resonance frequencies and Q-factor. Thus it includes means to measure the frequency response of said coaxial resonator within a frequency range including the waveguide mode $TE_{11}$ of said coaxial resonator, The coaxial insert wherein said coaxial insert is mounted to the pipe wall through at least one support legs being positioned outside said chosen cylindrical or annular volume, and one electrically conductive fin is positioned extending in the longitudinal direction at least partially into the region annular volume between the support legs and the antenna. This way the fin affects the resonance conditions in its position by damping the field and thus removing modes propagating in the annular volume in the tangential direction. In order to avoid interference problems the fin should be positioned outside the plane defined by the antenna and pipe axis in the annular volume. As is seen in the drawings angles in the range of 90° is preferred, but other solutions may be possible, e.g. depending on the number of fins and antennas.

This way the salinity of the fluid may thus be found by analyzing the resonance properties. The fluid may be a multiphase flow, e.g. containing water such as sea water having a certain salinity.

The measuring means is preferably adapted to measure the frequency response in a frequency range including at least said coaxial waveguide mode $TE_{11}$, and a coaxial TEM mode resonance.

At least two antennas may according to a preferred embodiment of the invention be positioned in a radial plane perpendicular to the radial plane defined by the fin, and on opposite sides of the insert in said pipe, each of which may emit and/or receive signals from the annular volume.

The insert has a shape having a minimum distance from the pipe wall at the position of said volume, e.g as a conical shape along the pipe direction.

Preferably the at least one conductive fin is constituted by at least one support leg extending a chosen length into said volume.

The insert may be mounted between at least two legs extending from the pipe wall, the legs being positioned in the plane at equal distances between said antenna. Where three legs, one of which being positioned in said plane may be preferably for stabilization purposes. Four legs, two of which being positioned in said plane, may also be used and may be advantageous for other purposes, e.g. as illustrated in FIG. 5.

The system may include calculating means for calculating the conductivity in said cylindrical volume based on the frequency of said $TE_{11}$ resonance mode. The calculating means may preferably be adapted to calculate the conductivity in said volume, said calculations including the TEM and $TE_{11}$ resonance properties measured in said cylindrical volume.

The invention claimed is:

1. A system for measuring electrical characteristics of a fluid flowing through a section of a pipe, the system comprising:
   a coaxial resonator, formed by an essentially coaxial insert in the pipe defining an annular volume between a part of the essentially coaxial insert and a pipe wall, the essentially coaxial insert and the pipe wall being made from an electrically conductive material;
   at least one antenna adapted to emit electromagnetic signals into and receive electromagnetic signals from the coaxial resonator;
   wherein a frequency response of the coaxial resonator is measured within a frequency range including a waveguide mode $TE_{11}$ of the coaxial resonator; and
   wherein the essentially coaxial insert is mounted to the pipe wall through at least one support leg being positioned outside the annular volume, and an electrically conductive fin is positioned at least partially in the annular volume, the electrically conductive fin being positioned in a radial plane, the radial plane being different from planes defined by positions of the at least one antenna and a plane defined by an axis of the annular volume.

2. The system according to claim 1, wherein the frequency response is measured in a frequency range including at least the waveguide mode $TE_{11}$, and a coaxial TEM mode resonance.

3. The system according to claim 1, wherein at least two antennas are positioned in a radial plane perpendicular to the radial plane defined by the electrically conductive fin, and on opposite sides of the essentially coaxial insert in the pipe.

4. The system according to claim 1, wherein the essentially coaxial insert has a shape having a minimum distance from the pipe wall at a position of the annular volume.

5. The system according to claim 4, wherein the essentially coaxial insert has a conical shape along a direction of the pipe.

6. The system according to claim 1, wherein the electrically conductive fin is constituted by at least one support leg extending a chosen length into the annular volume.

7. The system according to claim 6, wherein the essentially coaxial insert is mounted between at least two legs extending from the pipe wall, the at least two legs being positioned in the radial plane at equal distances between the at least one antenna.

8. The system according to claim 7, wherein the essentially coaxial insert is mounted between three legs, one of which being positioned in the radial plane.

9. The system according to claim 7, wherein the essentially coaxial insert is mounted between four legs, two of which being positioned in the radial plane.

10. The system according to claim 1, wherein the system calculates conductivity in the annular volume based on a resonance frequency of the TE11 resonance mode.

11. The system according to claim 10, wherein the calculations include TEM and TE11 resonance properties measured in the annular volume.

12. The system according to claim 1, comprising support legs made from an electrically conducting material.

* * * * *